United States Patent [19]

Knoll et al.

[11] Patent Number: 4,859,766

[45] Date of Patent: Aug. 22, 1989

[54] PURIFIED APPETITE-REGULATING SUBSTANCES OF BIOLOGICAL ORGIN, THEIR ANTIBODIES, IMMUNOCOMPLEXES OF THE APPETITE—REGULATING SUBSTANCES FORMED WITH THE ANTIBODIES AND PROCESSES FOR PREPARING SAME

[75] Inventors: József Knoll; Sándor Harmath, both of Budapest; János Nagy, Szentendre; Berta Knoll, Budapest, all of Hungary

[73] Assignee: Richter Gedeon Vegyeszeti, Budapest, Hungary

[21] Appl. No.: 134,403

[22] Filed: Dec. 17, 1987

[30] Foreign Application Priority Data

Dec. 17, 1986 [HU] Hungary .............................. 5254/86

[51] Int. Cl.$^4$ ................... C07K 15/14; A61K 35/16; A61K 37/02
[52] U.S. Cl. ................................... 530/380; 424/85.5; 424/101; 514/8; 514/21; 530/395; 530/830
[58] Field of Search .................... 424/85, 101, 85.8; 530/380, 830, 395; 514/8, 21

[56] References Cited

U.S. PATENT DOCUMENTS 4,294,825 10/1981 Knoll et al. ...................... 514/21 X
4,430,264 2/1984 Knoll et al. ...................... 530/830 X
4,588,685 5/1986 Knoll et al. ...................... 530/380 X Primary Examiner—Howard E. Schain
Attorney, Agent, or Firm—Herbert Dubno; Jonathan Myers

[57] ABSTRACT

The selective appetite-regulating substances satietin and satietin-D had up to the present been prepared from human or animal blood serum or plasma by ultrafiltration, gel chromatography, treatment with trichloroacetic acid, affinity chromatography and optionally treatment with a proteolytic enzyme.

According to the invention, satietin and satietin-D are obtained in a purified form by using immunoabsorption. Being glycoproteins, both satietin and satietin-D form antibodies (antisatietin and antisatietin-D, respectively) in the living organism and can be isolated from the blood and bound to a gel column. For the preparation of satietin and satietin-D, respectively, the human or animal blood plasma or serum is subjected to ultrafiltration and the ultrafiltrate, containing in addition to satietin and satietin-D other constituents with a molecular weight below 50000 daltons, is contacted with the gel column. The antibody bound to the gel column forms with satietin or satietin-D, respectively, an immunocomplex remaining on the column while the other constituents of the ultrafiltrate can be eluted by a buffer. Then, the immunocomplex is cleaved, whereby satietin or satietin-D, respectively, can be eluted in a purified form from the column. The column containing the antibody may repeatedly be used.

4 Claims, No Drawings

PURIFIED APPETITE-REGULATING SUBSTANCES OF BIOLOGICAL ORGIN, THEIR ANTIBODIES, IMMUNOCOMPLEXES OF THE APPETITE—REGULATING SUBSTANCES FORMED WITH THE ANTIBODIES AND PROCESSES FOR PREPARING SAME

The invention relates to the purified form of selective appetite-regulating substances of biological origin, namely the active substances satietin and satietin-D which are obtained by the method of immunoabsorption.

The invention relates further to the antibody of satietin (hereinafter called antisatietin) and to the antibody of satietin-D (hereinafter called antisatietin-D) recognizing the determinant groups of satietin or satietin-D, respectively.

According to a further aspect of the invention, there is provided a process for preparing antisatietin and antisatietin-D, which comprises parenterally introducing satietin or satietin-D, respectively, to a living organism commonly used for immunization and then, after passing of an appropriate period, isolating antisatietin or antisatietin-D, respectively, in a manner known per se from the antiserum of a suitable specifity and avidity.

The invention relates further to the immunocomplexes of satietin with antisatietin and of satietin-D with antisatietin-D as well as a process for preparing these immunocomplexes, which comprises contacting satietin with antisatietin and satietin-D with antisatietin-D, respectively, under conditions providing the desired binding.

The immunocomplexes of the invention are formed on a solid phase, preferably on a gel column, suitably on an activated and equilibrated gel column. Satietin or satietin-D, respectively may be liberated from these immunocomplexes by an agent which is known to be useful for cleaving immunocomplexes. Thus, satietin or satietin-D, respectively, can be prepared in a purified, i.e. native form possessing the properties according to the natural origin.

The invention relates further to a process for preparing satietin and satietin-D, respectively, in a purified form from human or animal blood serum or plasma, which comprises subjecting human or animal blood serum or plasma to consecutive ultrafiltration, gel chromatography, treatment with trichloroacetic acid, affinity chromatography and then, if desired, to a treatment with a proteolytic enzyme, preferably with trypsin or chymotrypsin, controlling the purity and homogeneity of the thus obtained product by using an immunochemical method, preferably immunoelectrophoresis, adding an adjuvant to the immunochemically homogeneous product, parenterally introducing this product together with the adjuvant to a living organism commonly used for immunization and then, after passing of a suitable period, isolating the polyclonal monovalent antisatietin and antisatietin-D from the antiserum obtained from the blood of the living organism and having a suitable avidity and specifity, binding them to a solid phase, preferably to an activated and equilibrated gel, then letting an equilibrated ultrafiltrate containing the native components with a molecular weight below 50000 daltons of the human or animal blood serum or plasma to flow through the gel column containing the antibodies, selectively desorbing satietin or satietin-D from the immunocomplex of satietin formed with antisatietin or from that of satietin-D formed with antisatietin-D, respectively, from the column and finally recovering the respective eluates and optionally subjecting them to lyophilization.

Both satietin and satietin-D are active substances specifically acting on the satiety centre and regulating the appetite.

A new-type selective appetite-regulating substance prepared from human or animal blood serum is known from the British patent specification No. 2,056,993.

According to the U.S. Pat. No. 4,430,264, this substance (its commercial name is "satietin") obtained by ultrafiltration and gel chromatography of the serum and plasma was subjected to an additional chemical operation for further purification. Thus, the activity of this substance was enhanced by treating it with trichloroacetic acid and using affinity chromatography. As a further development, the process was supplemented with novel elements (see the U.S. Pat. No. 4,588,685) providing the isolation of a chemically uniform, selective appetite-regulating substance (its commercial name is "satietin-D") which differs from satietin in its physical characteristics. This latter process comprises a further purification step in which the substance, isolated through ultrafiltration and gel chromatography, then treated with trichloroacetic acid, and subjected to affinity chromatography as described in the two patent specifications mentioned hereinbefore, is treated with trypsin and chymotrypsin. This method was based on the recognition that satietin is a glycoprotein which resists a proteolytic enzyme treatment and which retains its biological activity, while the accompanying contaminations are decomposed by trypsin and chymotrypsin and can be removed.

Now, it has been found in the course of a further development of the above processes that the separation of satietin and satietin-D representing native constituents of the human or animal blood can be prepared more simply and simultaneously more specifically by isolating satietin or satietin-D, respectively, from the ultrafiltrate of human or animal blood serum or plasma by using immunoabsorbent chromatography which is a specific type of the affinity chromatography.

The process of the present invention will be discussed hereinafter in detail.

(1) Satietin or satietin-D, respectively, is prepared by using, for example the processes described in the British patent specification No. 2,056,993 and in the U.S. Pat. Nos. 4,430,264 and 4,588,685. In addition to the previously employed methods, the homogeneity and purity of these products are controlled in an immunochemical way, preferably by electrophoresis [Int. Arch. All. Appl. Immunol. 7, 103 (1955)], more particularly by a two-dimension immunoelectrophoresis [Anal. Biochem. 10, 358 (1965); and Clin. Sci. 35, 403 (1968)] by using polyvalent antibodies precipitating human serum proteins, respectively, monovalent antibodies precipitating known serum proteins. Thus, the eventually contaminating proteins can be identified and the purity of the products can be confirmed. The immunochemically homogeneous product is buffered, an adjuvant, preferably incomplete Freund's adjuvant is added and the mixture is parenterally administered to a living organism commonly used for immunization, preferably to rabbits or goats. Suitably, the animals are subjected to several inoculations for producing polyclonal monovalent antibodies against satietin or satietin-D, i.e. antisatietin or antisatietin-D, respectively. After an appropriate period, when the antiserum proves to have sufficient avidity and precipitating properties on the basis of blood samples, the animals are sacrified and bled, the blood obtained is centrifuged and the antibody is isolated from the supernatant, i.e. from the antiserum in the usual way by using e.g. gel filtration and/or preparative electrophoresis and/or fractionation with organic solvents and/or salting out and/or ion-exchange chromatography, preferably salting out and ion-exchange chromatography.

(2) The polyclonal monovalent antisatietin or antisatietin-D, respectively, prepared according to (1) above is bound to a solid phase, preferably to an activated and equilibrated gel, particularly to Sepharose gel, and an appropriate column is prepared therefrom. Cyanogen bromide can preferably be used as an activating agent. Thereupon, the gel column containing the antibody is equilibrated by using a buffer solution of pH 2.5 to 10, preferably a Tris buffer [a mixture of tris(hydroxymethyl)aminomethane and hydrochloric acid, pH 8.5], a buffer containing glycine and hydrochloric acid (pH 2.5) or a borate buffer (0.025 molar aqueous solution, pH 8.8).

Then, a calculated amount of the human or animal blood serum or plasma is filtered on a membrane filter permeable up to a molecular weight of 50000 daltons. (For the preparation of satietin e.g. Amicon UM 10 while for satietin-D e.g. Amicon hollow fibre $H_{10}P_{10}$ membrane filter is used.) Subsequently, the ultrafiltrate containing all the native human or animal blood serum or plasma constituents with a molecular weight below 50000 daltons is concentrated to about one-fifth of its volume, the thus obtained concentrated ultrafiltrate is equilibrated with the same buffer previously used for equilibrating the gel column. The equilibrated ultrafiltrate is then introduced to the gel column containing the antibody.

The satietin or satietin-D content of the ultrafiltrate is bound in the form of an immunocomplex by antisatietin or antisatietin-D, respectively, previously bound to the gel; these are only bound while other native human or animal blood serum or plasma constituents with a molecular weight below 50000 daltons are eluted from the column by using the buffer, preferably a borate buffer, previously employed for equilibrating both the gel column and the ultrafiltrate. When the eluate is observed by UV spectrometry to be free from proteins, an agent commonly used for cleaving the immunocomplexes such as guanidine hydrochloride, an aqueous solution of urea or preferably ammonium rhodanide is introduced to the gel column containing the immunocomplex, whereby the binding of satietin to antisatietin or satietin-D to antisatietin-D is cleaved and satietin or satietin-D, respectively, can selectively be desorbed from the column. The fractions obtained from the gel are collected, made free from salts by dialyzing against distilled water and, if desired, lyophilized. The biological activity of the lyophilized active substance is determined according to the method described in the British patent specification No. 2,056,993.

The main advantage of the process of the invention is that the isolation of native satietin and satietin-D from the ultrafiltrate of human or animal blood serum or plasma can be performed in a substantially more simple way, i.e. by using the method of immunoabsorption which is milder and more specific than those employed up to now. Thus, satietin and satietin-D obtained in a purified form possess the properties corresponding to their natural origin, in opposition to those prepared according to the prior art. The biological activity of these active substances is the same as that of satietin san satietin-D, respectively, prepared according to the processes of the prior art. Before starting the process of the invention, the product required for immunization has practically only once to be prepared according to one of the known processes. The process of the invention is highly economic since the gel column containing the antibody may be used very much times with the same result. The invention makes possible to increase the scale of working up of ultrafiltrates.

The invention is illustrated in detail by the aid of the following non-limiting Examples.

EXAMPLE 1

Preparation of purified satietin (a) Rabbits are immunized by using in serial inoculations satietin prepared as described in the British patent specification No. 2,056,993 or U.S. Pat. No. 4,430,264, supplemented with the incomplete Freund's adjuvant. In defined intervals blood samples are taken and the specifity and avidity of the antisera are controlled by immunoelectrophoresis. When the strength of the antiserum is sufficient, the immunized donors are bled and the blood obtained is centrifuged to obtain the antiserum as supernatant.

To 100 ml of antiserum, 25 g of solid ammonium sulfate are added under continuous stirring. After standing for one hour, the mixture is centrifuged and the precipitate formed is separated from the supernatant. The precipitate is washed several times with an 1.75 molar aqueous ammonium sulfate solution and the precipitate containing antisatietin is separated by repeated centrifugation. Thereafter, the precipitate is first dialyzed against water and then against 0.05 molar aqueous sodium acetate solution at 4° C. This dialysis requires a few days, whereupon the solution is centrifuged to remove a little amount of precipitate formed.

A DEAE-Sephadex column is prepared by swelling the dry gel in a 0.05 molar aqueous sodium acetate solution and then preparing a gel bed of suitable dimension. The dialysate prepared as described above is layered onto the gel bed, the fractions flowing through the column are collected, then the combined fractions are salted out by adding 25 g of solid ammonium sulfate calculated for 100 ml of the fraction volume. The precipitate is separated from the supernatant by centrifuging and then dialyzed against a phosphate buffer of pH 7.2. The dialysate is concentrated and again dialyzed against 0.1 molar aqueous sodium carbonate solution at pH 8.8 at 4° C.

(b) 50 ml of AH-Sepharose 48 gel activated by cyanogen bromide is washed several times with 0.1 molar aqueous sodium carbonate buffer (8.8), then a 25% aqueous glutaraldehyde solution is added to this gel to ensure a 2.5% final concentration of glutaraldehyde and the mixture is let stand for one hours. The glutaraldehyde solution is removed by filtering the gel through a glass filter, then the gel is washed with a 0.1 molar aqueous sodium carbonate solution (pH 8.8).

Thereafter, the dialysate prepared according to (a) containing antisatietin is mixed with the gel, stirred for one additional hour at 4° C. and let stand for 16 hours. Then the gel is washed several times with a 0.1 molar aqueous sodium carbonate buffer (pH 8.8).

After this, the gel is washed several times with 0.2 molar aqueous ethanolamine solution and then made free from ethanolamine by washing several times with 0.1 molar aqueous sodium carbonate buffer. Subsequently, the gel is washed with 5 molar aqueous guanidine hydrochloride solution and then, the medium of the gel is displaced by a 0.025 molar borate buffer (pH 8.4).

After filling into a column, a gel bed of a given volume is prepared from the gel which is then equilibrated with 0.025 molar aqueous borate buffer (pH 8.4).

(c) Human blood serum is filtered through an Amicon UM 10 membrane filter which is permeable up to a molecular weight of 50000 daltons. The thus obtained ultrafiltrate is dialyzed against 0.025 molar aqueous borate buffer (pH 8.4). The dialysate is applied to the gel bed prepared according to (b) and the fractions taken from the column are collected. Satietin is taken up from the filtrate by antisatietin (which is bound to the gel); other unbound constituents of biological origin having a molecular weight below 50000 daltons, particularly serum protein fractions, can be removed by eluting with a 0.025 molar borate buffer (pH 8.4).

After controlling by UV spectrometry that no protein is contained in the eluate, the satietin is desorbed from the immunocomplex bound to the gel column by using two volumes (as calculated for the volume of the gel bed) of 3 molar aqueous ammonium rhodanide solution.

Satietin desorbed from the column is made free from ammonium rhodanide by dialysis against water, then the dialysate is lyophilized and its activity is determined by using the method described in the British specification No. 2,056,993.

EXAMPLE 2

Preparation of purified satietin-D

The process of Example 1 is followed, except that instead of satietin, satietin-D prepared according to the U.S. Pat. No. 4,588,685 is used in step a) and instead of Amicon UM 10, Amicon $H_{10}P_{10}$ hollow fibre is used as membrane filter in step c).

EXAMPLE 3

Preparation of purified satietin

The process of Example 1 is followed, except that goats are immunized instead of rabbits.

EXAMPLE 4

Preparation of purified satietin-D

The process of Example 2 is followed, except that goats are immunized instead of rabbits.

We claim:

1. A process for the preparation of a selective appetite-regulating substance of biological origin selected from the group consisting of Satietin and Satietin-D, in purified form, which comprises the steps of:
    (a) providing Satietin or Satietin-D obtained from human or animal blood serum or plasma, in impure form;
    (b) adding an adjuvant to the impure Satietin or Satietin-D and parenterally administering same to a mammalian subject to immunize said mammalian subject to form an antiserum containing polyclonal monovalent antibodies against Satietin or Satietin-D, designated Antisatietin or Antisatietin-D respectively in the blood of the mammalian subject;
    (c) removing the blood from the mammalian subject, centrifuging the blood to obtain the antiserum as a supernatent, and isolating from the antiserum Antisatietin or Antisatietin-D;
    (d) preparing an activated and equilibrated gel chromatographic column;
    (e) binding the Antisatietin or Antisatietin-D to the gel chromatographic column by layering same onto the gel bed of the gel chromatographic column;
    (f) equilibrating the gel chromatographic column containing Antisatietin or Antisatietin-D by passing a buffer solution at a pH of 2.5 to 10 therethrough;
    (g) ultrafiltering human or animal blood serum or plasma through a membrane filter permeable up to a molecular weight of 50,000 daltons to obtain a ultrafiltrate containing all native human or animal blood serum or plasma constituents with a molecular weight below 50,000 daltons;
    (h) equilibrating the ultrafiltrate with the same buffer employed in step (f);
    (i) introducing the equilibrated ultrafiltrate into the gel chromatographic column following the step (f) to selectively bind Satietin or Satietin-D contained in the ultrafiltrate to Antisatietin or Antisatietin-D bound to the gel chromatographic column to form an immunocomplex of Satietin-Antisatietin or Satietin-D-Antisatietin-D;
    (j) eluting the native human or animal blood serum or plasma constituents other than Satietin or Satietin-D through the gel chromatographic column by passing the buffer solution previously employed during steps (f) and (h) therethrough;
    (k) following step (j), passing an eluant having the ability to cleave the Satietin-Antisatietin or Satietin-D-Antisatietin-D complex bound to the gel chromatographic column to desorb selectively Satietin or Satietin-D thereby forming an eluate containing Satietin or Satietin-D; and
    (l) recovering the eluate containing Satietin and Satietin-D.

2. A process as claimed in claim 1, according to step (i), which comprises forming the immunocomplex on a Sepharose gel column.

3. A process as claimed in claim 1, according to step (f), which comprises equilibrating the gel column with a borate buffer and activating it by using cyanogen bromide.

4. A process as claimed in claim 1, according to step (k), which comprises liberating satietin and satietin-D, respectively, from their immunocomplexes bound to the gel column by using an aqueous ammonium rhodanide solution.

* * * * *